US012048692B2

(12) United States Patent
Barnes et al.

(10) Patent No.: US 12,048,692 B2
(45) Date of Patent: *Jul. 30, 2024

(54) METHODS FOR TREATING CHRONIC OBSTRUCTIVE PULMONARY DISEASE

(71) Applicant: THERAVANCE BIOPHARMA R&D IP, LLC, South San Francisco, CA (US)

(72) Inventors: Christopher Noel Barnes, South San Francisco, CA (US); Glenn D. Crater, South San Francisco, CA (US); Edmund J. Moran, South San Francisco, CA (US); Srikanth Pendyala, South San Francisco, CA (US)

(73) Assignee: THERA VANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/137,919

(22) Filed: Apr. 21, 2023

(65) Prior Publication Data

US 2023/0255952 A1    Aug. 17, 2023

Related U.S. Application Data

(63) Continuation of application No. 17/953,036, filed on Sep. 26, 2022, now abandoned, which is a continuation of application No. 16/555,216, filed on Aug. 29, 2019, now Pat. No. 11,484,531.

(60) Provisional application No. 62/724,805, filed on Aug. 30, 2018.

(51) Int. Cl.
    A61K 31/444    (2006.01)
    A61K 9/00      (2006.01)
    A61K 31/135    (2006.01)
    A61P 11/06     (2006.01)
    A61K 45/06     (2006.01)

(52) U.S. Cl.
    CPC .......... *A61K 31/444* (2013.01); *A61K 9/0078* (2013.01); *A61K 31/135* (2013.01); *A61P 11/06* (2018.01); *A61K 45/06* (2013.01)

(58) Field of Classification Search
    None
    See application file for complete search history.

(56) References Cited

U.S. PATENT DOCUMENTS

| | | | |
|---|---|---|---|
| 6,777,423 B2 | 8/2004 | Banholzer et al. | |
| 6,878,721 B1 | 4/2005 | Cuenoud et al. | |
| 7,288,657 B2 | 10/2007 | Mammen et al. | |
| 7,345,175 B2 | 3/2008 | Mammen et al. | |
| 7,439,393 B2 | 10/2008 | Box et al. | |
| 7,488,827 B2 | 2/2009 | Laine et al. | |
| 7,491,736 B2 | 2/2009 | Mammen et al. | |
| 7,498,440 B2 | 3/2009 | Laine et al. | |
| 7,521,041 B2 | 4/2009 | Mammen et al. | |
| 7,550,595 B2 | 6/2009 | Mammen et al. | |
| 7,585,879 B2 | 9/2009 | Mammen et al. | |
| 7,700,777 B2 | 4/2010 | Axt et al. | |
| 7,727,984 B2 | 6/2010 | Konetxki et al. | |
| 7,803,812 B2 | 9/2010 | Mammen et al. | |
| 7,910,608 B2 | 3/2011 | Mammen et al. | |
| 7,960,551 B2 | 6/2011 | Chudasama et al. | |
| 8,017,783 B2 | 9/2011 | Mammen et al. | |
| 8,034,946 B2 | 10/2011 | Mammen et al. | |
| 8,053,448 B2 | 11/2011 | Mammen et al. | |
| 8,101,766 B2 | 1/2012 | Chao et al. | |
| 8,138,345 B2 | 3/2012 | Hughes et al. | |
| 8,173,815 B2 | 5/2012 | Mammen et al. | |
| 8,242,137 B2 | 8/2012 | Axt et al. | |
| 8,273,894 B2 | 9/2012 | Mammen et al. | |
| 8,377,965 B2 | 2/2013 | Axt et al. | |
| 8,541,451 B2 | 9/2013 | Woollam | |
| 8,557,997 B2 | 10/2013 | Mammen et al. | |
| RE44,874 E | 4/2014 | Box et al. | |

(Continued)

FOREIGN PATENT DOCUMENTS

| | | |
|---|---|---|
| WO | WO 2005/087738 | 9/2005 |
| WO | WO 2006/099165 | 9/2006 |
| WO | WO 2011/008809 | 1/2011 |

OTHER PUBLICATIONS

Gold PM. "The 2007 Gold Guidelines: A Comprehensive Care Framework". Respiratory Care. 2009; 54(8):1040-1049. (Year: 2009).*
Al-Showair et al., "Can all patients with COPD use the correct inhalation flow with all inhalers and does training help?", Respiratory Medicine, 101:2395-2401 (2007).
Ari, "Jet, Ultrasonic, and mesh nebulizers: An evaluation of nebulizers for better clinical outcomes" Eurasian Journal of Pulmonology; 16:1-7 (2014).

(Continued)

*Primary Examiner* — Leslie A. Royds Draper
(74) *Attorney, Agent, or Firm* — Sheppard Mullin Richter & Hampton LLP

(57) ABSTRACT

Methods for treating chronic obstructive pulmonary disease (COPD) in a patient are disclosed. In the methods, a patient having COPD is selected for treatment based on the patient's peak inspiratory flow rate (PIFR) and percent predicted force expiratory volume in one second ($FEV_1$); and a bronchodilator is administered to the selected patient using a nebulizer. Administration of a bronchodilator to patients having low PIFR and a percent predicted $FEV_1$ less than 50 percent using a nebulizer as the inhalation delivery device provides significantly greater improvements in trough $FEV_1$ and trough forced vital capacity (FVC) compared to administration of a bronchodilator to such patients using a dry powder inhaler.

14 Claims, No Drawings

(56) References Cited

U.S. PATENT DOCUMENTS

| | | | |
|---|---|---|---|
| 8,716,313 | B2 | 5/2014 | Axt et al. |
| 8,754,225 | B2 | 6/2014 | Colson |
| 8,912,334 | B2 | 12/2014 | Mammen et al. |
| 8,921,395 | B2 | 12/2014 | Axt et al. |
| 8,921,396 | B2 | 12/2014 | Woollam |
| 9,226,896 | B2 | 1/2016 | Woollam |
| 9,249,099 | B2 | 2/2016 | Axt et al. |
| 9,283,183 | B2 | 3/2016 | Mammen et al. |
| 9,415,041 | B2 | 8/2016 | Woollam |
| 9,452,161 | B2 | 9/2016 | Mammen et al. |
| 9,656,993 | B2 | 5/2017 | Axt et al. |
| 9,765,028 | B2 | 9/2017 | Woollam |
| 9,926,272 | B2 | 3/2018 | Mammen et al. |
| 10,100,013 | B2 | 10/2018 | Woollam |
| 10,106,503 | B2 | 10/2018 | Mammen et al. |
| 10,343,995 | B2 | 7/2019 | Mammen et al. |
| 10,550,081 | B2 | 2/2020 | Woollam |
| 10,570,092 | B2 | 2/2020 | Mammen et al. |
| 10,577,347 | B2 | 3/2020 | Axt et al. |
| 11,008,289 | B2 | 5/2021 | Woollam |
| 11,247,969 | B2 | 2/2022 | Mammen et al. |
| 11,390,603 | B2 | 7/2022 | Axt et al. |
| 11,484,531 | B2 * | 11/2022 | Barnes .............. A61K 31/135 |
| 2004/0045546 | A1 | 3/2004 | Hirsh et al. |
| 2007/0112027 | A1 | 5/2007 | Axt et al. |
| 2010/0048622 | A1 | 2/2010 | Axt et al. |
| 2016/0166506 | A1 | 6/2016 | Gerhart et al. |
| 2018/0179161 | A1 | 6/2018 | Mammen et al. |
| 2018/0186740 | A1 | 7/2018 | Woollam |
| 2022/0009890 | A1 | 1/2022 | Woollam |
| 2022/0306579 | A1 | 9/2022 | Mammen et al. |
| 2022/0306580 | A1 | 9/2022 | Woollam |
| 2022/0388981 | A1 | 12/2022 | Axt et al. |

OTHER PUBLICATIONS

Atkins, "Dry powder inhalers: An overview", Respiratory Care, 50(10):1304-1312 (Oct. 2005).
Barnes et al., "Defining repeatability limits for measuring peak inspiratory flow rates in clinical trials", Am J Respir Crit Care Med, 199:A1130 (2019).
Barnes. Chronic obstructive pulmonary disease. N Engl J Med. Jul. 27, 2000;343(4):269-80.
Broeders et al., "The course of inhalation profiles during an exacerbation of obstructive lung disease", Respiratory Medicine, 98:1173-1179 (2004).
Casaburi et al., "The spirometric efficacy of once-daily dosing with tiotropium in stable COPD", Chest, 118:1294-1302 (2000).
Chodosh et al., "Effective delivery of particles with the HandiHaler dry powder inhalation system over a range of chronic obstructive pulmonary disease severity", Journal of Aerosol Medicine, 14(3):309-315 (2001).
Clinical trial entry NCT01704404. ClinicalTrials.gov. Submission dated May 12, 2017.
Clinical trial entry NCT02109172. ClinicalTrials.gov. Submission dated Jan. 17, 2017.
PCT International Preliminary Report for PCT/US2019/048764 dated Oct. 25, 2019.
PCT Written Opinion for PCT/US2019/048764 dated Oct. 25, 2019.
DeLaCruz et al., Trial in progress: a 52-week, randomized, double-blind, placebo-controlled, parallel group phase 3 trial to evaluate the safety and tolerability of a nebulized long-acting muscarinic antagonist (revenfenacin) in study participants with COPD. Chest 2016; 150:866A.
Donohue et al., "A 6-month, placebo-controlled study comparing lung function and health status changes in COPD patients treated with tiotropium or salmeterol", Chest, 122:47-55 (2002).
Duarte et al., "Spirometry Measurement of Peak Inspiratory Flow Identifies Suboptimal Use of Dry Powder Inhalers in Ambulatory Patients with COPD.", Chronic obstructive pulmonary diseases, 6(3):246-255 (2019).
FDA. Food and drug administration , guidance for industry: nasal spray and inhalation solution, suspension, and spray drug products—chemistry, manufacturing, and controls documentation. 2002.
Ferguson et al., "Improvements in lung function with nebulized revefenacin in the treatment of patients with moderate to very severe COPD: Results from two replicate phase III clinical trials", Chronic Obstr Pulm Dis., 6(2):154-165 (2019).
Ghosh et al., "Peak inspiratory flow rate in chronic obstructive pulmonary disease: Implications for dry powder inhalers", Journal of Aerosol Medicine and Pulmonary Drug Delivery, 30(6): 381-387 (2017).
Ghosh et al., "Prevalence and factors associated with suboptimal peak inspiratory flow rates in COPD", International Journal of COPD, 14:585-595 (2019).
Global Initiative for Chronic Obstructive Lung Disease. Pocket Guide to COPD Diagnosis, Management, and Prevention. A Guide for Health Care Professionals. 2017 Edition (Updated Dec. 2017). pp. 1-37. Publisher: Global Initiative for Chronic Obstructive Lung Disease, Inc. (Fontana, WI).
Haumann et al., Dose-ranging study of once-daily TD-4208, an inhaled long-acting muscarinic antagonist (LAMA) in patients with Chronic Obstructive Pulmonary Disease (COPD), 19 Am. J. Respir. Crit. Care Med. (2015). Poster Abstract.
Hauptfleish, et al. An oral sodium citrate-citric acid non-particulate buffer in humans, Brit. J. Anaesthesia. 1996; 77(5):642-644.
Heo, "Revefenacin: First Global Approval", Drugs, (2019), vol. 79, pp. 85-91.
Janssens et al., "Inspiratory flow rates at different levels of resistance in elderly COPD patients", Eur Respir J, 31:78-83 (2008).
Jarenback et al., Bronchodilator response of advanced lung function parameters depending on COPD severity, Int'l J. Chron. Obstr. Pulm. Dis. 2016; 11:2939-2950.
Kondo et al., "Profiles of inhaled flow from dry powder inhalers in subjects unfamiliar with the devices", Jpn J Pharm Health Care Sci, 40(6): 344-351 (2014).
Loh et al., "Suboptimal inspiratory flow rates are associated with chronic obstructive pulmonary disease and all-cause readmissions", Ann Am Thorac Soc, 14(8): 1305-1311 (Aug. 2017).
Loh et al., Personalization of device therapy—prime time for peak inspiratory flow rate. Chronic Obstr Pulm Dis. 2017; 4(3): 172-176.
Mahler et al., "Comparison of dry powder versus nebulized beta-agonist in patients with COPD who have suboptimal peak inspiratory flow rate", Journal of Aerosol Medicine and Pulmonary Drug Delivery, 27(2): 103-109 (Nov. 2014).
Mahler et al., "Nebulized versus dry powder long-acting muscarinic antagonist bronchodilators in patients with COPD and suboptimal peak inspiratory flow rate", Chronic Obstr Pulm Dis., 6(4):321-331 (2019).
Mahler et al., "Prevalence and COPD phenotype for a suboptimal peak inspiratory flow rate against the simulated resistance of the diskus dry powder inhaler", Journal of Aerosol Medicine and Pulmonary Drug Delivery, 26(3): 174-179 (2013).
Mahler, "Peak inspiratory flow rate as a criterion for dry powder inhaler use in chronic obstructive pulmonary disease", Ann Am Thorac Soc, 14(7): 1103-1107 (Jul. 2017).
Mahler, "Peak Inspiratory Flow Rate: An Emerging Biomarker in Chronic Obstructive Pulmonary Disease.", American journal of respiratory and critical care medicine, 199(12):1577-1579 (2019).
Malmberg et al., "Inspiratory flows through dry powder inhaler in chronic obstructive pulmonary disease: Age and gender rather than severity matters", International Journal of COPD, 5:257-262 (2010).
Miller et al., "Standardization of spirometry", Eur Respir J, 26: 319-338 (2005).
Muralidharan et al., "Dry powder inhalers in COPD, lung inflammation and pulmonary infections", Expert Opinion on Drug Delivery, 12(6):947-962 (2015).
Nicholls et al., A randomized crossover, 7-day study of once-daily Td 4208, a long-acting muscarinic antagonist, in subjects with COPD. Am. J. Resp. Crit. Care Med. 2014; 189. A6003. Poster abstract.
Price et al., "Physiological predictors of peak inspiRatory flow using Observed lung function resultS (POROS): evaluation at

(56) References Cited

OTHER PUBLICATIONS discharge among patients hospitalized for a COPD exacerbation.", International journal of chronic obstructive pulmonary disease, 13:3937-3946 (2018).
Pudi et al., "A 28-Day, Randomized, Double-Blind, Placebo-Controlled, Parallel Group Study of Nebulized Revefenacin in Patients with Chronic Obstructive Pulmonary Disease". Respiratory Research. 2017; 18:182. Published Online Nov. 2, 2017.
Pudi et al., Trials in progress : two 12-week, randomized, double-blind, placebo-controlled, parallel-group Phase 3 trials of a nebulized long-acting muscarinic antagonist (revenfenacin) in study participants with moderate to very severe COPD. Obstructive Lung Diseases. Oct. 26, 2016; 150(4):Supplement 825A.
Pulido-Rios et al., In vivo pharmacological characterization of TD-4208, a novel lung-selective inhaled muscarinic antagonist with sustained bronchoprotective effect in experimental animal models, Journal of Pharmacology and Experimental Therapeutics. Aug. 2013; 345: 241-250.
Quinn et al., "Pharmacodynamics, pharmacokinetics and safety of revefenacin (TD-4208), a long-acting muscarinic antagonist, in patients with chronic obstructive pulmonary disease (COPD): Results of two randomized, double-blind, phase 2 studies", Pulmonary Pharmacology & Therapeutics, 48: 71-79 (2018).
Ramlal et al., The effect of bronchodilators administered via aerochamber or a nebuzlier on inspiratory lung function parameters. Resp. Med. 2013; 107(9):1393-1399.
Revefenacin Peak Inspiratory Flow Rate (PIFR) Study in COPD. ClinicalTrials.gov. First Posted: Mar. 29, 2017 (Updated Sep. 25, 2018). pp. 1-5. Publisher: U.S. National Library of Medicine (Bethesda, MD).
Rogliani et al., "Optimizing drug delivery in COPD: The role of inhaler devices", Respiratory Medicine, 124:6-14 (2017).
Sanders, "Guiding inspiratory flow: Development of the in-check DIAL G16, a tool for improving inhaler technique", Pulmonary Medicine, vol. 2017, Article ID 1495867, 7 pages (2017).
Seheult et al., "Investigating the relationship between peak inspiratory flow rate and volume of inhalation from a diskus inhaler and baseline spirometric parameters: a cross-sectional study", SpringerPlus, 3: 496 (2014).
Sharma et al., "Prevalence of low peak inspiratory flow rate at discharge in patients hospitalized for COPD exacerbation", Chronic Obstr Pulm Dis, 4(3): 217-224 (2017).
Taffet et al., Considerations for managing chronic obstructive pulmonary disease in the elderly. Clinical interventions in aging. 2014; 9:23-30.
Tashkin, "A review of nebulized drug delivery in COPD", International Journal of COPD, 11: 2585-2596 (2016).
Theravance Biopharma Press Release, Feb. 27, 2018.
Thorat, "Formulation and product development of nebuliser inhaler: An overview", International Journal of Pharmaceutical Science and Research, 1(5): 30-35 (Jul. 2016).
Van Der Palen, "Peak inspiratory flow through diskus and turbuhaler, measured by means of a peak inspiratory flow meter (In-check DIAL)", Respiratory Medicine, 97: 285-289 (2003).
Vestbo et al., "Global Strategy for the Diagnosis, Management, and Prevention of Chronic Obstructive Pulmonary Disease: GOLD Executive Summary". Am J Respir Crit Care Med. 2013; 187(4):347-365.
Vogelmeier et al., "Global strategy for the diagnosis, management, and prevention of chronic obstructive lung disease 2017 report", Am J Respir Crit Care Med, 195(5): 557-582 (Mar. 2017).
Yawn et al., Practical aspects of inhaler use in the management of chronic obstructive pulmonary disease in the primary care setting. International Journal of COPD. 2012; 7:495-502.
Taiwan Clinical-Care Guidelines for Chronic Obstructive Pulmonary Disease. Health Promotion Administration, Ministry of Health and Welfare, Taiwan, ROC. (Mar. 2017). Second Section of Chapter Four. 19 pages.
ClinicalTrials.gov ID NCT05165485. Phase 4 COPD and Suboptimal Inspiratory Flow Rate (PIFR-2). Last Updated Dec. 19, 2023. 10 pages.
Theravance Biopharma Announces Results from the Phase 4 Yupelri® PIFR-2 Study in Patients with Severe to Very Severe Chronic Obstructive Pulmonary Disease (COPD). PRNewswire. Jan. 5, 2024. 3 pages.
Abbreviated Clinical Study Report, Revefenacin, YUPELRI®, Study 0180, Theravance Biopharma, Inc. May 13, 2024, 49 pages.
Johns, David P. et al. "Diagnosis and early detection of COPD using spirometry" Journal of Thoracic Disease, Pioneer Bioscience Publishing Company, vol. 6, No. 11, Nov. 2014, 1557-1569.

\* cited by examiner

METHODS FOR TREATING CHRONIC OBSTRUCTIVE PULMONARY DISEASE

CROSS-REFERENCE TO RELATED APPLICATIONS

This application is a continuation application of U.S. Ser. No. 17/953,036, filed on Sep. 26, 2022, which is a continuation application of U.S. Ser. No. 16/555,216, filed on Aug. 29, 2019, now U.S. Pat. No. 11,484,531, which claims the benefit of U.S. Provisional Application No. 62/724,805, filed on Aug. 30, 2018; the entire disclosures of which are incorporated herein by reference in their entireties.

BACKGROUND OF THE INVENTION

Field of the Invention

The present invention relates to methods for treating chronic obstructive pulmonary disease (COPD) in a patient. More specifically, in one of its aspects, the invention relates to methods for selecting a COPD patient for treatment based on the patient's peak inspiratory flow rate (PIFR) and percent predicted force expiratory volume in one second ($FEV_1$); and then administering a bronchodilator to the selected patient using a nebulizer.

State of the Art

COPD is a chronic inflammatory lung disease characterized by progressive persistent airflow obstruction. Bronchodilators, such as muscarinic receptor antagonists and β-adrenergic agonists, are commonly used to treat COPD. See, e.g., Vogelmeier, C. F. et al., *Am J Respir Crit Care Med*, 2017; 195(5), 557-582. Such bronchodilators are typically delivered to a patient in need of treatment using an inhalation delivery device, such as a dry powder inhaler, a metered dose inhaler or a nebulizer. See, e.g., Tashkin, D. P., *International Journal of COPD*, 2016; 11, 2585-2596. For many patients, any type of inhalation delivery device can be used to delivery an adequate dose of a bronchodilator. However, for COPD patients having a lower than normal inspiratory flow rate, nebulizers are sometimes recommended since these patients may be unable to generate a peak inspiratory flow rate sufficient for proper use of a dry powder inhaler. See, e.g., Mahler, D. A., *Ann Am Thorac Soc*, 2017; 14(7), 1103-1107; and Mahler, D. A. et al., *J Aerosol Med Pulm Drug Deliv*, 2014; 27(2), 103-109. Accordingly, use of a nebulizer for delivery of a bronchodilator has been suggested for COPD patients having low PIFR.

SUMMARY OF THE INVENTION

Surprisingly, it has now been discovered that low PIFR alone is not sufficient to predict which COPD patients will benefit from use of a nebulizer for delivery of a bronchodilator. In a clinical trial comparing the effects of bronchodilators delivered to COPD patients using either a nebulizer or a dry powder inhaler, it has unexpectedly been discovered that patients having both low PIFR and low percent predicted $FEV_1$ (<50%) achieved significantly greater improvements in trough $FEV_1$ and trough forced vital capacity (FVC) when a bronchodilator was administered using a nebulizer compared to a dry powder inhaler. In contrast, in patients having low PIFR and a percent predicted $FEV_1 \geq 50\%$, a significant difference in trough $FEV_1$ and FVC was not observed between patients using a nebulizer versus patients using a dry powder inhaler. Thus, it has now been discovered that COPD patients having low PIFR and a percent predicted $FEV_1 < 50\%$ will gain additional benefit from a bronchodilator if the bronchodilator is delivered to such patients using a nebulizer instead of a dry powder inhaler. This unexpected discovery can be used to select COPD patients for treatment with a bronchodilator using a nebulizer thereby improving the therapeutic outcome for such patients.

Accordingly, in one aspect, the present invention relates to a method for treating chronic obstructive pulmonary disease in a patient comprising: (a) selecting a patient having a peak inspiratory flow rate (PIFR) less than about 60 L/min and a percent predicted force expiratory volume in one second ($FEV_1$) less than about 50 percent; and (b) administering a bronchodilator to the selected patient using a nebulizer.

In another aspect, the present invention relates to a method comprising: (a) determining the peak inspiratory flow rate (PIFR) of the patient; (b) determining the percent predicted force expiratory volume in one second ($FEV_1$) of the patient; (c) selecting the patient for treatment with a bronchodilator administered using a nebulizer if the patient has a PIFR less than about 60 L/min and a percent predicted $FEV_1$ less than about 50 percent; and (d) administering the bronchodilator to the selected patient using the nebulizer.

Unless otherwise indicated, the following separate and distinct embodiments are applicable for each aspect of the invention described herein.

In one embodiment of the methods of this invention, the patient has a PIFR less than about 50 L/min; including less than about 40 L/min; such as less than about 30 L/min. In one embodiment, the patient has a percent predicted $FEV_1$ less than 40 percent; including less than 30 percent. In one embodiment, the patient has a PIFR in the range of about 20 L/min to less than about 60 L/min and a percent predicted $FEV_1$ in the range of from about 20 percent to less than about 50 percent.

In one embodiment, the bronchodilator employed in the methods of this invention is a muscarinic antagonist; a β-adrenergic receptor agonist; a muscarinic antagonist-β-adrenergic receptor agonist (MABA); or a combination of a muscarinic antagonist and a β-adrenergic receptor agonist.

In one embodiment, the bronchodilator is a muscarinic antagonist. In another embodiment, the bronchodilator is a muscarinic antagonist selected from aclidinium, glycopyrronium, ipratropium, revefenacin, tiotropium and umeclidinium; or a pharmaceutically acceptable salt thereof. In a particular embodiment, the muscarinic antagonist is revefenacin or a pharmaceutically acceptable salt thereof.

In one embodiment, the bronchodilator is a β-adrenergic receptor agonist. In another embodiment, the bronchodilator is a β-adrenergic receptor agonist is selected from albuterol, arformoterol, formoterol, indacaterol, levalbuterol, metaproterenol, salmeterol, terbutaline, and vilanterol; or a pharmaceutically acceptable salt thereof.

In one embodiment, the bronchodilator is a muscarinic antagonist-β-adrenergic receptor agonist (MABA). In a particular embodiment, the bronchodilator is batefenterol or a pharmaceutically acceptable salt thereof.

In one embodiment, the bronchodilator is a combination of a muscarinic antagonist and a β-adrenergic receptor agonist.

In another aspect, the present invention relates to a method for treating chronic obstructive pulmonary disease in a patient, the method comprising: (a) selecting a patient having a peak inspiratory flow rate (PIFR) less than about 60 L/min and a percent predicted force expiratory volume in one second ($FEV_1$) less than about 50 percent; and (b) administering a pharmaceutical composition comprising an aqueous solution of revefenacin or a pharmaceutically acceptable salt thereof to the selected patient using a nebulizer.

Unless otherwise indicated, the following separate and distinct embodiments are applicable for each aspect of the invention described herein.

In one embodiment, the pharmaceutical composition has a pH in the range of about 4.5 to about 5.5. In another embodiment, the pharmaceutical composition has a pH of about 4.8 to about 5.2; including about 5.

In one embodiment, the pharmaceutical composition is isotonic.

In one embodiment, the pharmaceutical composition further comprises a tonicity agent and a buffer. In another embodiment, the pharmaceutical composition further comprises sodium chloride, citric acid and sodium citrate.

In one embodiment, the pharmaceutical composition is sterile, isotonic and has a pH of about 5.

In one embodiment, the pharmaceutical composition comprises about 20 μg/mL to about 60 μg/mL of revefenacin or a pharmaceutically acceptable salt thereof. In another embodiment, the pharmaceutical composition comprises about 88 μg/3 mL of revefenacin or a pharmaceutically acceptable salt thereof. In another embodiment, the pharmaceutical composition comprises about 175 μg/3 mL of revefenacin or a pharmaceutically acceptable salt thereof.

In one embodiment, the pharmaceutical composition is administered using a jet nebulizer.

In another aspect, the present invention relates to a method for selecting a patient having COPD for treatment with a bronchodilator administered using a nebulizer, the method comprising (a) determining the peak inspiratory flow rate (PIFR) of the patient; (b) determining the percent predicted force expiratory volume in one second ($FEV_1$) of the patient; and (c) selecting the patient for treatment with a bronchodilator administered using a nebulizer if the patient has a PIFR less than about 60 L/min and a percent predicted $FEV_1$ less than about 50 percent.

In another aspect, the present invention relates to a method for selecting a nebulizer as the inhalation delivery device used to administer a bronchodilator to a patient having COPD, the method comprising (a) determining the peak inspiratory flow rate (PIFR) of the patient; (b) determining the percent predicted force expiratory volume in one second ($FEV_1$) of the patient; and (c) selecting a nebulizer to administer a bronchodilator to the patient if the patient has a PIFR less than about 60 L/min and a percent predicted $FEV_1$ less than about 50 percent.

Other aspects and embodiments of this invention are disclosed herein.

DETAILED DESCRIPTION OF THE INVENTION

In its various aspects and embodiments, the present invention provides methods relating to the treatment of COPD in a patient based on the patient's peak inspiratory flow rate (PIFR) and percent predicted force expiratory volume in one second ($FEV_1$).

Definitions

When describing the present invention, the following terms have the following meanings unless otherwise indicated.

The singular terms "a," "an" and "the" include the corresponding plural terms unless the context of use clearly dictates otherwise.

The term "about" means ±10 percent of the specified value.

The term "low peak inspiratory flow rate" or "low PIFR" means a peak inspiratory flow rate less than about 60 L/min. Low peak inspiratory flow rate is also referred to as suboptimal peak inspiratory flow rate.

The term "peak inspiratory flow rate" or "PIFR" means the maximal flow rate achievable from a forced inspiration with an open glottis starting from a position of full expiration, typically expressed in liters/minute.

The term "peak inspiratory flow rate less than about 60 L/min" means a peak inspiratory flow rate less than about 60 L/min against a resistance of about 23 $\sqrt{kPa} \cdot L^{-1} \cdot min \cdot 10^{-3}$ (e.g., against the simulated resistance of a DISKUS® device) or an equivalent thereof. Similarly, other terms such as "peak inspiratory flow rate less than about 50 L/min" and the like mean a peak inspiratory flow rate determined against a resistance of about 23 $\sqrt{kPa} \cdot L^{-1} \cdot min \cdot 10^{-3}$ (e.g., against the simulated resistance of a DISKUS® device) or an equivalent thereof.

The term "pharmaceutically-acceptable" means acceptable for administration to a patient (e.g., having acceptable safety for the specified usage).

The term "pharmaceutically-acceptable salt" means a salt prepared from an acid and a base (including zwitterions) that is acceptable for administration to a patient (e.g., a salt having acceptable safety for a given dosage regime).

The term "revefenacin" means 1-(2-{4-[(4-carbamoylpiperidin-1-yl)methyl]-N-methylbenzamido}ethyl) piperidin-4-yl N-([1,1'-biphenyl]-2-yl)carbamate (alternatively known as biphenyl-2-ylcarbamic acid 1-(2-{[4-(4-carbamoylpiperidin-1-ylmethyl)benzoyl]methylamino}ethyl)piperidin-4-yl ester) having chemical structure:

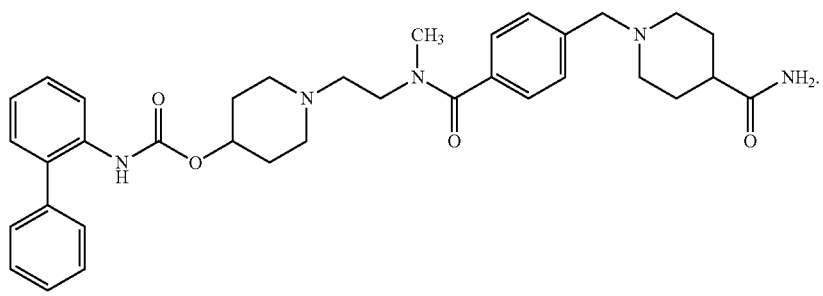 [SMILES: CN(CCN1CCC(OC(=O)Nc2ccccc2-c2ccccc2)CC1)C(=O)c1ccc(CN2CCC(C(N)=O)CC2)cc1]

As used herein, the term "revefenacin" is intended to include revefenacin (free base) and pharmaceutically acceptable salts of revefenacin unless otherwise indicated.

The term "therapeutically effective amount" means an amount sufficient to effect treatment when administered to a patient in need of treatment, e.g., the amount needed to obtain the desired therapeutic effect.

The term "treating" or "treatment" means ameliorating or suppressing the medical condition or disorder being treated; or alleviating the symptoms of the medical condition or disorder.

All other terms used herein are intended to have their ordinary meaning as understood by persons having ordinary skill in the art to which they pertain.

Bronchodilators

Any suitable bronchodilator can be used in the present invention. Representative examples of types or classes of bronchodilators suitable for use in the present invention include muscarinic antagonists; β-adrenergic receptor agonists; muscarinic antagonist-β-adrenergic receptor agonists (MABAs); and combinations of a muscarinic antagonist and a β-adrenergic receptor agonist.

In one embodiment, the bronchodilator is a muscarinic antagonist. The muscarinic antagonist can be a short-acting muscarinic antagonist (SAMA) or a long-acting muscarinic antagonists (LAMA). Representative examples of muscarinic antagonists include, but are not limited to, aclidinium, glycopyrronium, ipratropium, revefenacin, tiotropium, umeclidinium, and the like; and pharmaceutically acceptable salts thereof. Particular examples of pharmaceutically acceptable salts of muscarinic antagonists include aclidinium bromide, glycopyrronium bromide, ipratropium bromide, tiotropium bromide, umeclidinium bromide, and the like. In a particular embodiment, the muscarinic antagonist is revefenacin or a pharmaceutically acceptable salt thereof. In another particular embodiment, the muscarinic antagonist is glycopyrronium or a pharmaceutically acceptable salt thereof; including glycopyrronium bromide.

The muscarinic antagonists employed in the present invention are commercially available or can be prepared by well-known procedures. For example, methods for preparing muscarinic antagonists are described in U.S. Pat. Nos. 6,777,423; 7,288,657; 7,488,827; 7,498,440; 8,754,225; and the like.

In another embodiment, the bronchodilator is a β-adrenergic receptor agonist. The β-adrenergic receptor agonist can be a short-acting β-adrenergic receptor agonist (SABA) or a long-acting β-adrenergic receptor agonist (LABA). Representative examples of β-adrenergic receptor agonists include, but are not limited to, albuterol, arformoterol, formoterol, indacaterol, levalbuterol, metaproterenol, olodaterol, salmeterol, terbutaline, vilanterol, and the like; or a pharmaceutically acceptable salt thereof. Particular examples of pharmaceutically acceptable salts of β-adrenergic receptor agonists include albuterol sulfate, arformoterol tartrate, formoterol fumarate, indacaterol maleate, levalbuterol hydrochloride, metaproterenol sulfate, olodaterol hydrochloride, salmeterol xinafoate, terbutaline sulfate, vilanterol trifenatate, and the like. In a particular embodiment, the β-adrenergic receptor agonist is selected from arformoterol, formoterol, indacaterol, olodaterol, salmeterol, vilanterol; or a pharmaceutically acceptable salt thereof.

The β-adrenergic receptor agonists employed in the present invention are commercially available or can be prepared by well-known procedures. For example, methods for preparing β-adrenergic receptor agonists are described in U.S. Pat. Nos. 6,878,721; 7,439,393; 7,727,984; RE44,874; and the like.

In another embodiment, the bronchodilator is a muscarinic antagonist-β-adrenergic receptor agonist (MABA). In a particular embodiment, the bronchodilator is batefenterol and the like; or a pharmaceutically acceptable salt thereof. Particular examples of pharmaceutically acceptable salts of MABAs include batefenterol succinate and the like.

The MABAs employed in the present invention are commercially available or can be prepared by well-known procedures. For example, methods for preparing MABAs are described in U.S. Pat. Nos. 7,345,175; 7,960,551; 8,101,766; 8,138,345; and the like.

In one embodiment, the bronchodilator is a combination of a muscarinic antagonist and a β-adrenergic receptor agonist. Representative combinations include, but are not limited to, albuterol and ipratropium; tiotropium and olodaterol; revefenacin and formoterol; umeclidinium and vilanterol; and the like; and pharmaceutically acceptable salts thereof.

Pharmaceutical Compositions

Any pharmaceutical composition suitable for use in a nebulizer can be employed in the present invention. Typically, such pharmaceutical compositions comprise a bronchodilator and a pharmaceutically acceptable carrier. Representative pharmaceutically acceptable carriers include, but are not limited to, water and water/ethanol mixtures. The bronchodilator may be present in the pharmaceutically acceptable carrier as a solution or a suspension. Such pharmaceutical compositions may also optionally contain one or more additional excipients. See, e.g., Thorat, *IJPSR*, 2016; 1(5): 30-35.

Representative types of excipients that may be employed in the pharmaceutical composition include, by way of example, buffers, preservatives, co-solvents, suspending agents, surfactants, tonicity adjusting agents, humectants, cation chelating agents, and the like. Examples of buffers (used to buffer the pH of the formulation) include, but are not limited to, citric acid, sodium citrate, sodium phosphate and the like. Examples of preservatives (used, e.g., to prevent microbial growth in the formulation) include, but are not limited to, benzalkonium chloride, ethanol, propylene glycol, benzyl alcohol, chlorobutanol, methyl paraben and the like. Examples of co-solvents (used to improve solubility) include, but are not limited to, ethanol, PEG 400, propylene glycol and the like. Examples of suspending agents (used to increase the viscosity and suspendability of a suspension) include, but are not limited to, carboxymethyl cellulose, sodium carboxymethyl cellulose, and the like. Examples of surfactants (used to increase the suspendability and stability of a suspension) include, but are not limited to, polysorbate 20, polysorbate 80 and the like. Examples of tonicity adjusting agents (used to adjust the tonicity of the formulation) include, but are not limited to, sodium chloride, dextrose and the like. Examples of humectants (used to maintain moisture in the formulation) include, but are not limited to, glycerin and the like. Examples of cation chelating agents (used to form chelates with ions present in the formulation and to increase stability) include, but are not limited to disodium EDTA and the like. Additionally, pH adjusting agents may be used to adjust the pH of the formulation. Examples of pH adjusting agents include, but art not limited to, sodium hydroxide, hydrochloric acid, sulfuric acid and the like.

In general, when an excipient is employed in the pharmaceutical composition, the excipient will be used in an amount sufficient to perform its desired function. Such an amount is either known in the art or is readily determined by routine experimentation. For example, the amount of tonicity agent present in the pharmaceutical composition typically ranges from about 0.1 to about 5 wt. % based on the total weight of the composition; including about 0.5 to about 3 wt. %; such as about 1 to about 2 wt. %. The amount of buffer or buffering agent present in the pharmaceutical composition typically ranges from about 0.1 to about 5 wt. % based on the total weight of the composition; including about 0.5 to about 3 wt. %; such as about 1 to about 2 wt. %.

In one embodiment, the pharmaceutically composition comprises a bronchodilator and an aqueous carrier. In one embodiment, this pharmaceutical composition further comprises one or more excipients. In another embodiment, this pharmaceutical composition further comprises a buffer and a tonicity agent. In a particular embodiment, the pharmaceutical composition further comprises sodium citrate, citric acid and sodium chloride.

In one embodiment, the pharmaceutical composition is sterile.

In one embodiment, the pharmaceutical composition is isotonic.

In one embodiment, the pharmaceutical composition has a pH of about 4 to about 6. In another embodiment, the pharmaceutical composition has a pH of about 4.5 to about 5.5. In another embodiment, the pharmaceutical composition has a pH of about 4.8 to about 5.2; including about 5.

In one embodiment, the pharmaceutical composition is sterile, isotonic and has a pH of about 4.8 to about 5.2; including about 5.

A representative pharmaceutical composition for use in a nebulizer comprises an isotonic aqueous solution comprising from about 0.05 µg/mL to about 10 mg/mL of a bronchodilator; including about 10 µg/mL to about 100 µg/mL of the bronchodilator; or about 30 µg/mL to about 60 µg/mL of the bronchodilator. In one embodiment, this solution contains a tonicity agent comprising sodium chloride. In one embodiment, this solution contains a buffer comprising citric acid and sodium citrate. In one embodiment, this solution has a pH of about 4 to about 6; including about 4.8 to about 5.2; including about 5.

Typically, the pharmaceutical composition is prepared by dissolving the bronchodilator and any optional excipients in the pharmaceutically acceptable carrier and adjusting the pH of the composition to the desired pH using a pH adjusting agent. In one embodiment, the excipients are first dissolved in the carrier and the pH is adjusted, and then the bronchodilator is dissolved in the resulting composition. Alternatively, if the bronchodilator is not soluble in the carrier, the bronchodilator can be micronized and combined with a suitable composition to form a suspension of micronized particles.

Nebulizers

Any suitable nebulizer can be using in this invention including, by way of example, jet nebulizers, ultrasonic nebulizers and vibrating mesh nebulizers. See, e.g., Ari, *Eurasian J Pulmonol*, 2014; 16: 1-7 and Thorat, *IJPSR*, 2016; 1(5): 30-35. Jet nebulizers include, for example, (a) jet nebulizers with a corrugated tube; (b) jet nebulizers with a collection bag; (c) breath-enhanced jet nebulizers; and (d) breath-actuated jet nebulizers. Representative examples of jet nebulizers include, but are not limited to, the AKITA® JET nebulizer (Vectura, Chippenham, UK); the AEROECLIPSE® (Trudell Medical International, London, Ontario, Canada); the CIRCULAIRE® (Westmed INC, Tucson, AZ, USA); the InnoSpire Mini Compressor nebulizer (Philips Healthcare, Andover, MA, USA); the NEBU TECH® (Salter Labs, Arvin, CA, USA); the PARI LC PLUS®, and the PARI LC® Sprint (PARI, Starnberg, Germany); the TREK® S jet nebulizer (PARI, Midlothian, VA, USA); and the like. Representative examples of ultrasonic nebulizers include, but are not limited to, MICRO AIR® Electronic (Omron Healthcare, Bannockburn, IL, USA); MINIBREEZE™ Ultrasonic (Mabis, Waukegan, IL, USA); the FLPY™ (Convexity Scientific, Westport, CT, USA); and the like. Representative examples of vibrating mesh nebulizers include, but are not limited to, AEROGEN® Solo (Aerogen, Chicago, IL, USA); EFLOW® (PARI, Starnberg, Germany); and the like. Such nebulizers are used according to the manufacturer's instructions.

Determination of PIFR and Percent Predicted $FEV_1$

Peak inspiratory flow rate (PIFR) and percent predicted force expiratory volume in one second less ($FEV_1$) are determined using standard procedures known in the art. See, e.g., Sharma et al., *Chronic Obstr Pulm Dis.* 2017; 4(3): 217-224.

For example, PIFR can be determined using a handheld peak inspiratory flow meter, such as the IN-CHECK® DIAL device (Clement Clarke Ltd. Harlow, UK or Alliance Tech Medical, Granbury, TX, USA). See, e.g., Van der Palen, *Respr Med* 2003; 97: 285-289. When using the IN-CHECK® DIAL device, the resistance of the device is set to simulate the resistance of a dry powder inhaler (DPI) device, such as the DISKUS® device. The resistance of the DISKUS® device has been calculated to be 22.96 $\sqrt{kPa} \cdot L^{-1} \cdot min \cdot 10^{-3}$ or about 23 $\sqrt{kPa} \cdot L^{-1} \cdot min \cdot 10^{-3}$ (see, e.g., Kondo et al., *Jpn J Pharm Health Care Sci*, 40(6), 344-351 (2014)). Accordingly, in a particular embodiment, PIFR is determined against a resistance of about 23 $\sqrt{kPa} \cdot L^{-1} \cdot min \cdot 10^{-3}$. In another particular embodiment, PIFR is determined using the IN-CHECK® DIAL device with the resistance set to the DISKUS® setting or set to Med Low (ACCUHALER® or DISKUS®). When used according to the manufacturer's instructions, PIFR (L/min) is read from the scale on the IN-CHECK® DIAL device. Alternatively, PIFR can be determined using baseline spirometric parameters as described, e.g., in Seheult et al. *SpringerPlus* 2014, 3:496.

Those skilled in the art will appreciate that the PIFR determined for a given patient will vary depending on the method and the resistance used to measure PIFR and that, for purposes of the present invention, low PIFR includes equivalents of PIFR less than about 60 L/min when measured against a resistance of about 23 $\sqrt{kPa} \cdot L^{-1} \cdot min \cdot 10^{-3}$.

Percent predicted $FEV_1$ is determined by comparing measured $FEV_1$ for a patient with predicted $FEV_1$ for that patient based on the patient's age, race, height and gender (i.e., measured $FEV_1$/predicted $FEV_1 \times 100$=percent predicted $FEV_1$). $FEV_1$ is measured using a standard spirometry test or pulmonary function test which involves forcefully breathing out into a mouthpiece connected to a spirometer. See, e.g., Miller et al., *Eur Respir J*, 2005; 26: 319-338. Predicted $FEV_1$ is calculated based on age, race, height and gender using well-known procedures. For example, the Centers for Disease Control and Prevention provide an online calculator that can be used to determine predicted $FEV_1$ (www.cdc.gov/niosh/topics/spirometry/refcalculator.html).

Selection of a Patient or a Nebulizer for Treatment

In one aspect of the present invention, a patient having COPD is selected for treatment with a bronchodilator administered using a nebulizer if the patient has a PIFR less than about 60 L/min and a percent predicted $FEV_1$ less than about 50 percent. In another aspect of the invention, a nebulizer is selected as the inhalation delivery device used to administer a bronchodilator to a patient having COPD if the patient has a PIFR less than about 60 L/min and a percent predicted $FEV_1$ less than about 50 percent.

In one embodiment, PIFR is less than about 50 L/min. In another embodiment, PIFR is less than about 40 L/min. In another embodiment, PIFR is less than about 30 L/min. In one embodiment, percent predicted $FEV_1$ is less than about 40 percent. In another embodiment, percent predicted $FEV_1$ is less than about 30 percent. Particular embodiments include those where PIFR (L/min) and percent predicted $FEV_1$ (%) are about: <60 and <50; <50 and <50; <40 and <50; <60 and <40; <50 and <40; <40 and <40; <60 and <30; <50 and <30; <40 and <30, respectively. In another particular embodiment, the patient has a PIFR in the range of about 20 L/min to less than about 60 L/min and a percent predicted $FEV_1$ in the range of from about 20 percent to less than about 50 percent.

In one embodiment of the method, PIFR and percent predicted $FEV_1$ have been determined previously and the patient is selected based on such predetermined values. Alternatively, in another embodiment, the method includes the steps of determining PIFR and $FEV_1$ for a patient and then selecting the patient for treatment with a bronchodilator administered using a nebulizer inhaler if the patient has a PIFR less than about 60 L/min and a percent predicted $FEV_1$ less than about 50 percent.

Administration of the Bronchodilator to the Patient

Once a patient has been selected, the bronchodilator is administered to the selected patient using a nebulizer. The dose of the bronchodilator administered to the patient is typically determined by a physician based on the severity of the patient's condition and other factors, including the recommended or approved dose for the bronchodilator. Representative doses include, but are not limited to, about 5 μg to about 500 μg of the bronchodilator once or twice per day depending the bronchodilator. In one embodiment, the bronchodilator is revefenacin administered at a dose of about 88 μg once per day. In another embodiment, the bronchodilator is revefenacin administered at a dose of about 175 μg once per day. Once selected, the dose is administered using a nebulizer according to the manufacturer's instructions.

EXAMPLES

The following examples are provided to illustrate various representative embodiments and aspects of this invention and are not intended to limit the scope of this invention unless specifically indicated.

Example 1

Clinical Study Comparing a Bronchodilator Administered with Nebulizer Inhaler to a Bronchodilator Administered with Dry Powder Inhaler A 28-day, randomized, double-blind, double-dummy, parallel-group study was conducted to compare once-daily revefenacin (175 μg of revefenacin in 3 mL of an isotonic, sterile aqueous solution containing sodium chloride, citric acid, sodium citrate, and water for injection at pH 5.0) delivered using a nebulizer (Trek S jet nebulizer (PARI, Midlothian, VA, USA) with once-daily tiotropium (18 μg/day) delivered using a dry powder inhaler (Spiriva HandiHaler, Boebringer Ingelheim Pharmaceuticals, Inc., Ridgefield, CT, USA) on lung function in subjects with chronic obstructive pulmonary disease and a low peak inspiratory flow rate. Subjects with moderate to very severe COPD were allowed to use concurrent respiratory therapy with the exception of other inhaled anticholinergics. The primary endpoint of the study was the change from baseline in trough forced expiratory volume in one second ($FEV_1$) after the 28$^{th}$ dose. Secondary endpoints included the change from baseline in peak $FEV_1$, trough forced vital capacity (FVC), peak FVC and trough inspiratory capacity (IC) as well as the safety and tolerability of revefenacin 175 μg. Inclusion criteria were: age≥40 years; a smoking history≥10 pack years; a diagnosis of COPD (post-bronchodilator $FEV_1$≤80% predicted and FEV/FVC≤70%); peak inspiratory flow rate (PIFR)<60 L/min as measured by IN-CHECK® DIAL device with resistance set to DISKUS® at screening.

The baseline characteristics of the patients included in the study are shown in Table 1. The tiotropium and revefenacin groups were well-balanced on age, sex, race, body mass index (BMI), smoking history, use of inhaled corticosteroids/long-acting beta agonists (ICS/LABA), rating in modified Medical Research Council (mMRC) dyspnea scale, and their spirometry measurements.

TABLE 1

Key Demographics and Baseline Clinical Characteristics

|  | Tiotropium (N = 104) | Revefenacin (N = 102) |
|---|---|---|
| Age, mean (SD) | 65.1 (8.36) | 65.1 (7.94) |
| Sex (male), n (%) | 64 (61.5%) | 60 (58.8%) |
| Race (white), n (%) | 95 (91.3%) | 90 (88.2%) |
| BMI, mean (SD) | 27.3 (6.50) | 27.6 (6.85) |
| Current smoker (yes), n (%) | 50 (48.1%) | 46 (45.1%) |
| Concurrent ICS/LABA use (yes), n (%) | 57 (54.8%) | 54 (52.9%) |
| Post-ipratropium percent predicted $FEV_1$, mean (SD) | 37.1 (15.06) | 36.6 (16.17) |
| Post-ipratropium $FEV_1$ to FVC (ratio), mean (SD) | 0.43 (0.109) | 0.42 (0.114) |
| Baseline $FEV_1$ (in mL), mean (SD) | 0.93 (0.417) | 0.90 (0.493) |
| Baseline FVC, mean (SD) | 2.22 (0.696) | 2.15 (0.739) |
| Baseline IC, mean (SD) | 1.71 (0.600) | 1.65 (0.568) |
| Baseline PIFR (L/min), mean (SD) | 45.4 (11.21) | 45.3 (11.91) |
| Proportion of subjects with Baseline mMRC ≥2, n (%) | 78 (75.0%) | 76 (74.5%) |
| Proportion of subjects with ≤1 exacerbations in prior year, n (%) | 93 (89.4%) | 94 (92.2%) |

In this study, revefenacin (REV) (administered using a nebulizer) or tiotropium (TIC)) (administered using a dry powder inhaler) was dosed once-daily for 28 days, Peak inspiratory flow rates (best of three) were determined at screening, randomization and end of study using the IN-CHECK® DIAL device with the resistance set to a resistance equal or similar to the resistance associated with the DISKUS® device. $FEV_1$, FVC and IC were measured at baseline and/or peak on day 1 and on day 29. Safety was assessed via the collection of adverse events.

In the intention-to-treat (ITT) population, there were trends favoring revefenacin administered using a nebulizer over tiotropium administered using a dry powder inhaler for trough $FEV_1$ and FVC, but such trends did not meet statistical significance nor clinical relevance. However, in subjects with more severe airflow limitation ($FEV_1$<50% predicted), there were statistically significant and clinically relevant greater improvements in both trough $FEV_1$ and FVC for revefenacin administered using a nebulizer compared to tiotropium administered using a dry powder inhaler.

No differences in trough IC were noted. The data for trough $FEV_1$, FVC and IC are shown in Tables 2, 3 and 4, respectively.

TABLE 2

Trough Forced Expiratory Volume in One Second (Trough $FEV_1$)
(All Subjects PIFR <60 L/min)

| Trough $FEV_1$ | ITT Population | | % Predicted $FEV_1$ <50% Subpopulation | |
|---|---|---|---|---|
| | TIO 18 µg (N = 104) | REV 175 µg (N = 102) | TIO 18 µg (N = 81) | REV 175 µg (N = 80) |
| LS Mean (SE) | 47.3 (19.06) | 63.0 (20.17) | 27.5 (19.53) | 74.8 (20.85) |
| LS Difference (SE) | | 15.7 (22.35) | | 47.3 (21.76) |
| Nominal P-Value | | 0.4811 | | 0.0302 |

The data in Table 2 shows that a statistically significant difference in trough $FEV_1$ was observed for subjects treated with revefenacin (REV) administered using a nebulizer compared to subjects treated with tiotropium (TIO) administered using a dry powder inhaler if the subjects had both low PIFR (<60 L/min) and a percent predicted $FEV_1$<50%. Surprisingly, a statistically significant difference in trough $FEV_1$ was not observed for all subjects (ITT population) even though all subjects had low PIFR and the literature suggests that such a difference should be observed.

TABLE 3

Trough Forced Vital Capacity (Trough FVC)
(All Subjects PIFR <60 L/min)

| Trough FVC | ITT Population | | % Predicted $FEV_1$ <50% Subpopulation | |
|---|---|---|---|---|
| | TIO 18 µg (N = 104) | REV 175 µg (N = 102) | TIO 18 µg (N = 81) | REV 175 µg (N = 80) |
| LS Mean (SE) | 55.8 (36.62) | 125.4 (38.75) | 46.7 (43.56) | 146.5 (46.69) |
| LS Difference (SE) | | 69.6 (42.90) | | 99.9 (48.75) |
| Nominal P-Value | | 0.1040 | | 0.0407 |

The data in Table 3 shows that a statistically significant difference in trough FVC was observed for subjects treated with revefenacin (REV) administered using a nebulizer compared to subjects treated with tiotropium (TIO) administered using a dry powder inhaler if the subjects had both low PIFR (<60 L/min) and a percent predicted $FEV_1$<50%. Surprisingly, a statistically significant difference in trough FVC was not observed for all subjects (ITT population) even though all subjects had low PIFR.

TABLE 4

Trough Inspiratory Capacity (Trough IC)
(All Subjects PIFR <60 L/min)

| Trough IC | ITT Population | | % Predicted $FEV_1$ <50% Subpopulation | |
|---|---|---|---|---|
| | TIO 18 µg (N = 104) | REV 175 µg (N = 102) | TIO 18 µg (N = 81) | REV 175 µg (N = 80) |
| LS Mean (SE) | 84.1 (40.02) | 71.4 (42.33) | 76.0 (40.40) | 89.7 (42.85) |
| LS Difference (SE) | | −12.7 (47.38) | | 13.7 (45.43) |
| Nominal P-Value | | 0.7871 | | 0.7606 |

The data in Table 4 shows that a statistically significant difference in trough IC was not observed for subjects treated with revefenacin (REV) administered using a nebulizer compared to subjects treated with tiotropium (TIO) administered using a dry powder inhaler in either all subjects (ITT population) or in a subject subpopulation having both low PIFR (<60 L/min) and a percent predicted $FEV_1$<50%.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method for treating chronic obstructive pulmonary disease (COPD) in a patient with severe to very severe COPD, the method comprising:

(a) selecting a patient having a percent predicted forced expiratory volume in one second less than 50 percent; and (b) administering a pharmaceutical composition comprising an aqueous solution of revefenacin or a pharmaceutically acceptable salt thereof to the selected patient using a nebulizer;

wherein the patient has a low peak inspiratory flow rate.

2. The method of claim 1, wherein the low peak inspiratory flow rate is less than about 50 L/min.

3. The method of claim 1, wherein the patient has a percent predicted forced expiratory volume in one second less than about 40 percent.

4. The method of claim 1, wherein the patient has a percent predicted forced expiratory volume in one second less than about 30 percent.

5. The method of claim 1, wherein the patient has very severe COPD.

6. The method of claim 1, wherein the patient has a peak inspiratory flow rate in the range of about 20 L/min to less than about 60 L/min and a percent predicted forced a percent predicted forced expiratory volume in one second in the range of from about 20 percent to less than 50 percent.

7. The method of claim 1, wherein the pharmaceutical composition comprises about 175 µg/3 mL of revefenacin or a pharmaceutically acceptable salt thereof.

8. The method of claim 1, wherein the pharmaceutical composition has a pH in the range of about 4.5 to about 5.5.

9. The method of claim 1, wherein the pharmaceutical composition has a pH of about 4.8 to about 5.2.

10. The method of claim 1, wherein the pharmaceutical composition is isotonic.

11. The method of claim 1, wherein the pharmaceutical composition further comprises sodium chloride, citric acid and sodium citrate.

12. The method of claim 1, wherein the pharmaceutical composition is sterile, isotonic and has a pH of about 4.8 to about 5.2.

13. The method of claim 1, wherein the pharmaceutical composition is administered using a jet nebulizer.

14. The method of claim 1, wherein the pharmaceutical composition is administered once daily.

* * * * *

UNITED STATES PATENT AND TRADEMARK OFFICE
CERTIFICATE OF CORRECTION

| | |
|---|---|
| PATENT NO. | : 12,048,692 B2 |
| APPLICATION NO. | : 18/137919 |
| DATED | : July 30, 2024 |
| INVENTOR(S) | : Christopher Noel Barnes et al. |

It is certified that error appears in the above-identified patent and that said Letters Patent is hereby corrected as shown below:

On the Title Page

Item (73), please replace the text "THERA VANCE BIOPHARMA R&D IP, LLC, South San Francisco CA (US)" with -- THERAVANCE BIOPHARMA R&D IP, LLC, South San Francisco, CA (US) --.

At the bottom of the page, under Item (57) replace "14 Claims, No Drawings" with -- 13 Claims, No Drawings --.

In the Claims

Claim 1, Column 12, Line 50 to Claim 14, Column 14, Line 21, please replace:
"1. A method for treating chronic obstructive pulmonary disease (COPD) in a patient with severe to very severe COPD, the method comprising:
(a) selecting a patient having a percent predicted forced expiratory volume in one second less than 50 percent; and
(b) administering a pharmaceutical composition comprising an aqueous solution of revefenacin or a pharmaceutically acceptable salt thereof to the selected patient using a nebulizer;
wherein the patient has a low peak inspiratory flow rate.
2. The method of claim 1, wherein the low peak inspiratory flow rate is less than about 50 L/min.
3. The method of claim 1, wherein the patient has a percent predicted forced expiratory volume in one second less than about 40 percent.
4. The method of claim 1, wherein the patient has a percent predicted forced expiratory volume in one second less than about 30 percent.
5. The method of claim 1, wherein the patient has very severe COPD.
6. The method of claim 1, wherein the patient has a peak inspiratory flow rate in the range of about 20 L/min to less than about 60 L/min and a percent predicted forced a percent predicted forced expiratory volume in one second in the range of from about 20 percent to less than 50 percent.
7. The method of claim 1, wherein the pharmaceutical composition comprises about 175 µg/3 ml of revefenacin or a pharmaceutically acceptable salt thereof.

Signed and Sealed this
Twenty-ninth Day of October, 2024

Katherine Kelly Vidal
*Director of the United States Patent and Trademark Office*

CERTIFICATE OF CORRECTION (continued)
U.S. Pat. No. 12,048,692 B2

8. The method of claim 1, wherein the pharmaceutical composition has a pH in the range of about 4.5 to about 5.5.
9. The method of claim 1, wherein the pharmaceutical composition has a pH of about 4.8 to about 5.2.
10. The method of claim 1, wherein the pharmaceutical composition is isotonic.
11. The method of claim 1, wherein the pharmaceutical composition further comprises sodium chloride, citric acid and sodium citrate.
12. The method of claim 1, wherein the pharmaceutical composition is sterile, isotonic and has a pH of about 4.8 to about 5.2.
13. The method of claim 1, wherein the pharmaceutical composition is administered using a jet nebulizer.
14. The method of claim 1, wherein the pharmaceutical composition is administered once daily."
With:
-- 1. A method for treating chronic obstructive pulmonary disease (COPD) in a patient with severe to very severe COPD, the method comprising:
(a) selecting a patient having a percent predicted forced expiratory volume in one second less than 50 percent; and
(b) administering a pharmaceutical composition comprising an aqueous solution of revefenacin or a pharmaceutically acceptable salt thereof to the selected patient using a nebulizer;
wherein the patient has a low peak inspiratory flow rate.
2. The method of claim 1, wherein the low peak inspiratory flow rate is less than about 50 L/min.
3. The method of claim 1, wherein the patient has a percent predicted forced expiratory volume in one second less than about 40 percent.
4. The method of claim 1, wherein the patient has very severe COPD.
5. The method of claim 1, wherein the patient has a peak inspiratory flow rate in the range of about 20 L/min to less than about 60 L/min and a percent predicted forced expiratory volume in one second in the range of from about 20 percent to less than 50 percent.
6. The method of claim 1, wherein the pharmaceutical composition comprises about 175 μg/3 mL of revefenacin or a pharmaceutically acceptable salt thereof.
7. The method of claim 1, wherein the pharmaceutical composition has a pH in the range of about 4.5 to about 5.5.
8. The method of claim 1, wherein the pharmaceutical composition has a pH of about 4.8 to about 5.2.
9. The method of claim 1, wherein the pharmaceutical composition is isotonic.
10. The method of claim 1, wherein the pharmaceutical composition further comprises sodium chloride, citric acid and sodium citrate.
11. The method of claim 1, wherein the pharmaceutical composition is sterile, isotonic and has a pH of about 4.8 to about 5.2.
12. The method of claim 1, wherein the pharmaceutical composition is administered using a jet nebulizer.
13. The method of claim 1, wherein the pharmaceutical composition is administered once daily. --.